United States Patent [19]

Masquelier

[11] Patent Number: 4,698,360

[45] Date of Patent: Oct. 6, 1987

[54] PLANT EXTRACT WITH A PROANTHOCYANIDINS CONTENT AS THERAPEUTIC AGENT HAVING RADICAL SCAVENGER EFFECT AND USE THEREOF

[75] Inventor: Jack Masquelier, Parc des Tourelles, France

[73] Assignees: Societe Civile d'Investigations Pharmacologiques d'Aquitaine, Bordeaux, France; Horphag Overseas Ltd., St. Peter Port, Guernsey, Great Britain

[21] Appl. No.: 721,434

[22] Filed: Apr. 9, 1985

[51] Int. Cl.$^4$ .................................................. A61K 31/35
[52] U.S. Cl. ..................................................... 514/456
[58] Field of Search ........................ 424/195.1; 514/456

[56] References Cited

U.S. PATENT DOCUMENTS 3,436,407  4/1969  Masquelier .......................... 549/400

FOREIGN PATENT DOCUMENTS 1300869  7/1982  France .

OTHER PUBLICATIONS

Fartas et al, "Flavonids and Bioflavonoids, 1981, Studies in Organic Chem. Amsterdam, 1982.
Munro, Organization Mondicals de la Santé, Anthocyanins, 1977.
Masqueliner et al, Int. J. Vit. Nat. Res. 49:307–311, 1979.
Maridonneau et al, Chem. Abst. 97: 160662y, 1982.

Primary Examiner—Johnnie R. Brown
Assistant Examiner—John W. Rollins, Jr.

[57] ABSTRACT

The invention provides a method for preventing and fighting the harmful biological effects of free radicals in the organism of warm blooded animals and more especially human beings, namely cerebral involution, hypoxia following atherosclerosis, cardiac or cerebral infarction, tumour promotion, inflammation, ischaemia, alterations of the synovial liquid, collagen degradation, among others. The method consists in administering to said animals and especially to human beings an amount, efficient against said effects, of a plant extract with a proanthocyanidins content which has a radical scavenger effect, the extract being in the form of a medicament and coming more especially from the bark of conifers.

7 Claims, No Drawings

PLANT EXTRACT WITH A PROANTHOCYANIDINS CONTENT AS THERAPEUTIC AGENT HAVING RADICAL SCAVENGER EFFECT AND USE THEREOF

BACKGROUND OF THE INVENTION

1. Field of the Invention

The present invention relates to the use of a plant extract with a proanthocyanidins content as therapeutic agent with radical scavenger effect. It also relates to the use of pharmaceutical compositions containing this extract as active ingredient.

The medicaments of the present invention are obtained by extracting raw plant materials complying with different criteria:

1. A proanthocyanidins content,
2. Easy and permanent raw material supplies at low cost,
3. Absence of natural or artificial toxic constituents.

The bark of conifers, in particular pine bark such as that of the maritime pine (Pinus maritima), forms a first class material in this respect. Other conifers (refer to Jack Masquelier and Pierre Claveau, Naturaliste Can., 1966, 93, 345–348), such as the Canadian spruce (Tsuga canadensis), and many other arborescent or herbaceous plant species, contain proanthocyanidins and may then be used as raw material, if the criteria mentioned are complied with (Bate-Smith, E.C., Biochem. J., 1954, 58, 122–126; Bate-Smith, E.C., Lerner, N.H., Biochem.J., 1954, 58, 126–132). It will be essentially a question hereafter of a pine bark extract, but this expression should be considered as covering "any plant extract with a proanthocyanidins content". This content will vary with the plant material used to obtain the extract.

2. Prior Art

The use of maritime pine bark (Pinus Maritima), as raw material for extracting medicaments is described in patents by the same inventor (French Pat. Nos. 1 427 100 and 4482 M and the corresponding U.S. Pat. No. 3,456,407, which is included in the present description by reference).

Using an extraction process described in these patents, from pine bark can be obtained extracts which are used therapeutically for their action in the vascular field. Such properties place these medicaments among the vitamin P factors whose effect is to increase the resistance of small blood vessels and lower their permeability, so that hemorrhagic phenomena an oedema due to vascular fragility form the major uses for the products coming from pine bark.

DESCRIPTION OF THE INVENTION

Since these old patents were filed, scientific progress has led to a better knowledge of the chemical nature of the constituents which confer this therapeutic potential on pine bark extract. These substances are at present known under the name of "proanthocyanidins". It is under this new name, and whatever the original plant, that the substances responsible for the new medicinal activity claimed will be designated, which substances are identifiable by a specific test, which will be given hereafter.

The present invention relates in fact to a new therapeutic use of proanthocyanidins. This new use is the protection of warm blooded animals and in particular human beings with respect to the harmful biological effects caused by the release in the organism, more especially with aging, of free radicals, in particular those containing oxygen, that will be called hereinafter oxygen radicals. The protective effect is obtained because of the "radical scavenger effect" proper to the medicament.

In pine bark it is the proanthocyanidins which show the radical scavenger effect (R.S.E.). The proanthocyanidins form a class of natural polyphenols, defined by an exclusive property, namely the production of a red pigment (anthocyanidin) by the Bate-Smith reaction (Bate-Smith, E.C, Swain, T., Chemistry and Industry, 1953, pp. 377–378).

The Bate-Smith reaction, because of its specificity, is one of the processes used for detecting proanthocyanidins in a plant extract, and possibly for assessing the content thereof.

I.

RADICAL SCAVENGER EFFECT (R.S.E.) OF PROANTHOCYANIDINS

The R.S.E. has never been claimed in favor of proanthocyanidins. Although proanthocyanidins are polyphenols, it was not at all evident that they are endowed with R.S.E., whose intensity varies within wide limits depending on the molecular structure. The lag of knowledge in this connection is due to the difficulty in preparing chromatographically pure proanthocyanidins for use as standards during quantity determination. Only a few laboratories are at present capable of preparing such standards and they are not necessarily interested in the medical problems which these substances may resolve, which explains the lack of prior art in this field.

The R.S.E. of the pine bark extract may be demonstrated in vitro by different known tests, in particular by the TNB test (Nishikimi, M., Rav, N.A., Yagi, K., Biochem. Biophys. Res. Commun., 1972, 46, 849–854), according to which the oxygen radicals (particularly superoxide ions $O_2-\cdot$) have the property of reducing tetrazolium nitroblue (TNB) into formazan blue, whose quantity may be colorimetrically determined at 560 nm. In the presence of proanthocyanidins operating as $O_2-\cdot$ scavengers, reduction of the TNB is inhibited, which is demonstrated by a reduction of absorption at 560 nm.

With the TNB test, the pine bark extract shows an R.S.E. about 20 times higher than that of ascorbic acid used as reference.

Using a chicken embryo vascular tissue culture, the R.S.E. of the pine bark extract was also checked. Under certain conditions, these cultures degenerate rapidly and show in particular destruction of the membrane phospholipids under the action of the oxygen radicals (O.R.). The pine bark extract added to the medium maintains these cultures in a normal histologic condition. The same favorable result was observed on a human umbilical cord tissue culture.

Finally, the pine bark extract inhibits the tumour promotion process on the epiderm of mice. It is here also a question of an R.S.E., for the process brings into play the oxygen radicals as mentioned by Kensler, T. W., Bush, D. M., Kozumbo, W. J. in Science, 1983, 221, 75–77.

II.

BIOAVAILIBILITY OF PROANTHOCYANIDINS

Proanthocyanidins are included in the pycnogenols, a plant polyphenol chemical group, whose physical, chemical and biological properties have been studied in numerous works (see more especially J. Masquelier, J. Michaud, J. Laparra, and M. C. Dumon, Internat. J. Vit. Nutr. Res. 1979, 49, 307–311).

From the biological point of view, proanthocyanidins are characterized among the plant polyphenols by their lack of toxicity (see the above mentioned U.S. Pat. No. 3,436,407 which indicates an LD 50 of 3 g per kg per os, which excludes any risk of acute or chronic intoxication, the therapuetic doses being much smaller): used in therapeutical treatment for 30 years they have never given rise to any intoxication whatever. Non teratogenic, non mutagenic, they are also no nantigenic per se, which excludes any allergizing effect. In addition, they are stable (above mentioned US patent).

The bioavailability in warm blooded animals, which is related to the solubility in water, has been demonstrated by the oral administration of $^{14}C$ marked radioactive proanthocyanidins to rats and mice (J. Laparra, J. Michaud and J. Masquelier, Plantes médicin. et Phytoth. 1977, 11, 133).

Thus the fixing rate, the plasmatic half life and the nature of the privileged sites where the proanthocyanidins are fixed in the organism can be defined. It is the intact molecules which are involved during these measurements, since no rejection of $^{14}CO_2$ is detected in the air expired at the time when the animals are sacrificed.

In man, after the ingestion of 150 mg of pine bark extract in the form of capsules, in the following hour the presence of proanthocyanidins can be found in the saliva. The saliva gives in fact a positive Bate-Smith reaction which implies the secretion of non modified proanthocyanidins. This passing into the saliva thus proves the bioavailibility of proanthocyanidins in the human species.

Non antigenic, proanthocyanidins may however be detected also in the biological liquids and tissues by an immunological reaction. For that, a foreign molecule is grafted in a known way by hemisynthesis on the proanthocyanidins: the assembly acquires antigenic power. From that, using a known process, an antibody can be obtained which forms the most specific and most sensitive reagent which may be imagined for studying the development of proanthocyanidins in the animal organism and in particular in humans, by qualititive and quantitive determination in vivo, for example in the saliva, the blood, the urine, the cephalo-rachidian liquid, various secretions and excreta, as well as the tissues and organs.

PREFERRED EMBODIMENT

III.

Practical implementation of the invention. Example of pine bark.

The aim is to prepare a dry extract containing the proanthocyanidins of the raw material, to the exclusion of the condensed tannins which accompany them.

Whereas the extraction of chromatographically pure proanthocyanidins requires great know how and high performing equipment, the preparation of a dry titrated proanthocyanidin extract is within the scope of industry.

Extraction

A 100 kg of maritime pine bark reduced to a coarse powder are extracted with boiling water so as to collect 250 liters of liquid after having squeezed out the marc. The liquid cooled to 20° C. is filtered. To the filtrate sodium chloride is added up to saturation: instead of NaCl, 20% (weight/volume) of ammonium sulphate may also be added. The precipitate formed is eliminated by filtration. The filtrate is extracted thrice with ethyl acetate which is used each time at the rate of 1/10 of the volume of the aqueous phase. The ethyl acetate collected is dried on anhydrous $Na_2SO_4$ and brought back to 1/5 of its volume by distilltion under reduced pressure. It is then poured into three volumes of chloroform, while stirring mechanically. The proanthocyadins are precipitated. They are collected by filtration. They may be purified by redissolution in ethyl acetate and a new precipitation in chloroform. They are finally washed with chloroform and dried at reduced pressure in a heating chamber not exceeding 50° C.

General characteristics of the extract

A light beige colored powder, with astringent taste, very soluble in water and ethyl alcohol, insoluble in $CHCl_3$, $C_6H_6$, petroleum ether, ethyl ether. Can be kept indefinitely in a dry bottle at normal temperature. Identification: by the conventional Bate-Smith test: formation of an intense red coloration by heating to boiling point of an aqueous solution acidifed by 10% (volume/volume) of HCl. This solution stirred with isoamylic alcohol gives a supernatant layer having the physical and chemical properties of anthocyanidins.

Quantitative determination

To assess the proanthocyanidins content of pine bark extract, the specific affinity of these substances for collagen is used, no other constituent of the extract having the same affinity for the collagen of the hide. The method recommended in the leather industry (method of dosing tannins with hide powder) can be transposed to pine extracts. The principle is the following: an aqueous solution of known titre is prepared by dissolving a given weight of extract in water. This solution is placed in contact with the hide powder and this mixture is filtered, under well standardized conditions. With an aliquot volume of the filtrate, the residual dry extract is determined. The difference between the titre of the prepared solution and the dry extract rate represents the proantocyanidins content, which have remained fixed on the collagen of the hide powder. Bate-Smith (Phytochemistry, 1975, 14, 1107–1113) recommends this kind of technique for titrating the proanthocyanidins as a whole in a natural plant medium. Quantitative determinations based on spectral measurements or colored reactions come up against the presence of certain impurities giving false positive results.

Other analytical checks

These are routine techniques used for all medicinary extracts: search for pesticides, heavy metals, residual organic solvents, ash rates, chloride, sulphate, etc rates.

IV.

A Therapeutical indication

The proanthocyanidins titrated vegetable extracts are endowed with the "radical scavenger effect" (R.S.E.), The R.S.E. does not overcome aging, which is a biological process programmed in the genes, but it may prevent, attenuate or inhibit different harmful effects of aging caused by an excess of free radicals. On this are based the new indications claimed for such plant extracts.

1. Cerebral involution troubles in aged people.

With aged people, hypoxia of the tissues causes psychic and somatic troubles which are manifested in particular by ALZHEIMER's illness. Hypoxia produces an accumulation of reduced substrates (flavins, coenzymes, etc), whose autoxidation generates free radicals. These latter, if they go beyond the limits of the normal purifying mechanisms which bring enxymes into play, damage the cellular walls of the nervous tissue and lead to cerebral involution. To prevent the failure which is always possible of the purifying enzymes, it is then indicated to administrer a medicament with radical scavenger effect, provided that it is bioavailable. Proanthocyanadins fulfil the conditions. It has been discovered that they overcome the blood - brain barrier (J. Cahn and M. G. Borzeix, Sem. Hop. Paris, 1983, 59, No. 27-28, 2031-2034).

2. Hypoxia following atherosclerosis

The atheromatous illness, which does not occur only in old people, well represents however the picture of vascular aging and causes progressive hypoxia of the adjacent tissues. This hypoxia, through the free raicals which it generates, increases the lipid peroxidation, itself implied in the the pathogenesis of atherosclerosis. Through an identical mechanism, a modification of the platelet functions promoted by the free radicals causes the formation of thrombi which are at the basis of infarction. Proanthocyanidins are therefore indicated both for preventing the harmful effects of hypoxia following atheromatosis and also as agents for preventing cardiac or cerebral infarction.

3. Tumour promotion process

Oxygen radicals play an essential role in the tumour promotion process (in the promotion stage of carcinogenesis). Superoxide dismutase, tried as a protector, is a failure in this field for it is destroyed by the digestive enzymes and in any case it does not clear the cellular barrier very well (above mentioned article by KENSLER, T. W. et coll., SCIENCE, 1983, 221, 75-77). Similarly lipid peroxidation is implied in the transformation of the aromatic hydrocarbons into carcinogens (in the metabolism of polycyclic aromatic hydrocarbon derivatives to ultimate carcinogens) (DIX, T. A., MARNETT, L. J., SCIENCE, 1983, 221, 77-79). By their high R.S.E. combined with their rapid diffusion in the connective tissue, proanthocyanidins are therefore indicated as protectors against risks of cancerization by chemical, or physical (ionizing radiations), or biological (oncogens) agents).

4. Any illness generated by free radicals

The three preceding examples are in no wise limitative. Since the therapeutic effect is based on the scavenging of the free radicals, any pathology resulting from the direct or indirect action of these free radicals, or else following the temporary or definitive inefficiency of the normal enzymatic defense systems (peroxidase, catalase, superoxide-dismutase etc.) forms an indication for the therapeutic use of proanthocyanidins titrated extracts.

Cellular death forms the final step in aging on the cytologic scale. The free radicals, when they escape from the biological systems provided for eliminating them, attack first of all the fragile architecture of the membrane. The alterations thus produced accelerate cellular aging, characerized by the collapse of the primordial functions of the membrane system. Inflammation and ischaemia bring such a mechanism into play and so treatment by proanthocyanidins is indicated.

Similarly, alterations of the synovial liquid by depolymerization of hyaluronic acid during articular diseases as well as collagen degradation during so-called collagen diseases (for instance multliple sclerosis) spring from the action of free radicals and so enter into the therapeutic indications of proanthocyanidins.

V.

Posology, methods of administration and pharmaceutical forms

The proanthocyanidins may be administered by the digestive tract (orally or using suppositories), or parenterally (more especially intravenously), or cutaneously. For oral administration, the medicament is in the form of tablets, sugar coated pills, pellets, pill, capsules, cachets, drinkable ampoules. Intravenously, the unit dose of powder proanthocyanidins is dissolved, preferably at the time of use for better conservation of the efficiency of the medicament, in a separate ampoule of solvent (preferably physiological serum) and it must be injected slowly, because of a rapid reaction. Cutaneously, it may be used in the form of an ointment containing for example 0.5% by weight of proanthocyanidins in a non aqueous greasy excipient such as vaseline or lanolin.

The medicaments to be administered by the digestive tract or parenterally are in the form of doses containing an amount of the active proanthocyanidin substance corresponding to the daily dose or to a fraction thereof, depending on whether the medicament is to be administered once or several times per day.

Generally, for the preparation of the differnt pharmaceutical forms corresponding to the different possible methods of administration, the usual pharmaceutically acceptable carriers, excipients, envelopes, coatings, solvents and diluents may be used.

The posology, for oral administration, is generally from 1.5 to 3 mg per day per kilogram of body weight for warm blooded animals, which represents for an adult man weighing 70 kg a daily dose of about 100 to 200 mg of proanthocyanidins to be administered by unit doses for example of 50 to 100 mg so as to obtain R.S.E. in the above mentioned therapeutic indications.

For intravenous application in man, 5 mg of active substance (proanthocyanidins) to be dissolved in two milliliters of an injectable isotonic solvent at the time of use, is an efficient unit dose, to be injected once or twice per day, generally, which represents a daily dose of about 5 to 10 mg for an adult male.

The ointment with 0.5% of active substance, which is used for preventing and fighting certain tumours, may be applied once or several times per day on the regions to be treated.

I claim:

1. A method for preventing and fighting the harmful biological effect of free radicals in a warm blooded animals, including a human being, comprising administering the extracted proanthocyanidin content from a plant containing same, said extract having a bioavailable radical scavenger effect, to an animal exposed to said free radicals in an amount effective to reduce said harmful free radical effect, said extracted proanthocyanidin content being incorporated into a pharmaceutically acceptable medicament.

2. A method as claimed in claim 1, wherein the plant extract with a proanthocyanidin content is extracted from a proanthocyanidin-containing plant selected from the group consisting of arborescent and herbaceous plant species.

3. A method as claimed in claim 2, wherein the plant extract with a proanthocyanidin content comes from a conifer.

4. A method as claimed in claim 3, wherein the plant extract with a proanthocyanidin content comes from pine bark.

5. A method as claimed in claim 1, wherein said plant extract with a proanthocyanidin content is administered orally in an amount of about 1.5 to 3 mg per kilogram of body weight per day representing an amount of about 100 to 200 mg per day for an adult male weighing 70 kg, by slow intravenous administration in man in an amount of about 5 to 10 mg per day; and cutaneously in the form of an ointment containng about 0.5% by weight of proanthocyanidin applied at least once per day.

6. A method as claimed in claim 5, wherein said plant extract comes from conifer bark.

7. A method as claimed in claim 6, wherein said plant extract comes from pine bark.

* * * * *

REEXAMINATION CERTIFICATE (3366th)
United States Patent [19]
Masquelier

[11] B1 4,698,360
[45] Certificate Issued  Nov. 4, 1997

[54] PLANT EXTRACT WITH A PROANTHOCYANIDINS CONTENT AS THERAPEUTIC AGENT HAVING RADICAL SCAVENGER EFFECT AND USE THEREOF

[75] Inventor: Jack Masquelier, Parc des Tourelles, France

[73] Assignees: Societe Civile d'Investigations Pharmacologiques d'Aquitaine, Bordeaux, France; Horpah Overseas Ltd., St. Peter Port, Channel Islands; International Nutrition Company, Vaduz, Liechtenstein

Reexamination Request:
No. 90/004,223, Apr. 17, 1996

Reexamination Certificate for:
Patent No.: 4,698,360
Issued: Oct. 6, 1987
Appl. No.: 721,434
Filed: Apr. 9, 1985

[51] Int. Cl.$^6$ .................... A61K 31/35; A61K 35/78
[52] U.S. Cl. ............................. 514/456; 424/195.1
[58] Field of Search ................. 514/456; 424/195.1

[56] References Cited

U.S. PATENT DOCUMENTS

| | | | |
|---|---|---|---|
| 3,270,003 | 8/1966 | Van Blaricom et al. | 549/212 |
| 3,433,805 | 3/1969 | Kramer et al. | 540/400 |
| 3,436,407 | 4/1969 | Masquelier et al. | 540/400 |
| 3,549,661 | 12/1970 | Masquelier et al. | 540/400 |
| 3,888,990 | 6/1975 | Courbat et al. | 514/456 |
| 4,166,861 | 9/1979 | Bonati et al. | 514/456 |
| 4,255,336 | 3/1981 | Albert et al. | 540/400 |
| 4,268,517 | 5/1981 | Niebes et al. | 514/457 |
| 4,285,964 | 8/1981 | Niebes et al. | 514/457 |
| 4,376,781 | 3/1983 | Lietti et al. | 514/457 |
| 4,413,004 | 11/1983 | Lietti et al. | 514/456 |
| 4,515,804 | 5/1985 | Marti et al. | 514/456 |
| 4,613,672 | 9/1986 | Hara | 549/399 |
| 4,617,296 | 10/1986 | Albert et al. | 514/100 |
| 4,644,011 | 2/1987 | Ballenegger et al. | 514/456 |

FOREIGN PATENT DOCUMENTS 61-016982  7/1984  Japan ..................... 549/400

OTHER PUBLICATIONS

Shinji Uchida, et al., "Condensed Tannins Scavenge Active Oxygen Free Radicals", Med. Sci. Res. 15:831–832, 1987.
Jorge M. Ricardo da Silva, et al., "Oxygen Free Radicals Scavenger Capacity in Aquewous Models of Different Procyanidins from Grape Seeds", J. Agr. Food chem., 39:1549–1552, 1991.
R. Maffei Facino, et al., "Free Radicals Scavenging Action and Anti–enzyme Activities of Procyanidines from Vitis vinifera", Arzneim.–Forsch./Drug Res. 44(1), No. 5:592–601, 1994.
Joseph E. Pizzorno, Jr., N.D., et al., A Textbook of Natural Medicine, vol. 1, "Procyanidolic Oligomers", Bastyr College Publications, Seattle, Washington, pp. 795–797, 1993.

Richard A. Passwater, Ph.D., et al., "Pycnogenol The Super 'Protector' Nutrient", Keats Pub., pp. 50–51.
E. C. Bate–Smith, et al. "Identification of Leuco–Anthocyanins as 'Tannins' in Foods", Chem. and Indust. pp. 377–378, Apr. 18, 1953.
OPC in Practice, Bert Schwitters, "Bioflavanols and Their Application", pp 1–99, Jul. 30, 1993.
Harold Aaron, ed. (1968) "Requiem for Flavonoid Drugs", *The Medical Letter on Drugs and Therapeutics*, 10:9–10 (Exhibit 1).
E. C. Bate–Smith and T. Swain (1953) "Identification of Leuco–Anthocyanins as 'Tannins' in Foods", *Chemical and Industry*, 377–378 (Exhibit 2).
J. Baumann, F. Bruchhausen and G. Wurm (1981) "Flavonoids and Arachidonic Acid Metabolism", *Proceedings of the International Bioflavonoid Symposium*, Munich, FRG 411–419 (Exhibit 3).
J. Baumann, G. Wurm and F. Bruchhausen (1980) "Hemmung der Prostaglandinsynthetase durch Flavonide und Phenolderivate im Vergleich mit deren $O_2$- –Radikalfanger–eigenschaften", *Arch. Pharm.*, 313:330–337 (Exhibit 4).
L. Cavallini, A. Bindoli and N. Siliprandi (1978) "Comparative Evaluation of Antiperoxidative Action of Silymarin and Other Flavonoids", *Pharmacological Research Communications*, 10: 133–136 (Exhibit 5).
O. Danni, B. C. Sawyer and T. F. Slater (1977) "Effects of (+)–catechin in vitro and in vivo on distubances produced in rat liver endoplasmic reticulum by carbon tetrachloride" *Biochemical Society Transactions*, 5:1029–1032 (Exhibit 6).
N.P. Das (1971) "Studies on Flavonoid Metabolism", Biochemical Pharmacology, 20: 3435–3445 (Exhibit 7).
R. F. Del Maestro (1982) "Role of superoxide anion radicals in microvascular permeability and leukocyte behaviour", *Canadian Journal Of Physiology and Pharmacology*, 60:1406–1414 (Exhibit 8).
Rolando F. Del Maestro, Howard H. Thaw, Jakob Björk, Manfred Planker and Karl–E. Arfors (1980) "Free radicals as mediators of tissue injury", *Free Radicals in Medicine Biology*, 43–57 (Exhibit 9).
J.M. Gazave, J.L. Parrot, A. Saindelle and P. Canu, "Recherches sur la vitamine C2 (facteur d'economie de l'acide ascorbique)", *Laboratoire de Physiologie pathologique de L'Ecole Pratique des Hautes–Etudes*, 251 (Exhibit 10).

(List continued on next page.)

*Primary Examiner*—John Rollins

[57]  ABSTRACT

The invention provides a method for preventing and fighting the harmful biological effects of free radicals in the organism of warm blooded animals and more especially human beings, namely cerebral involution, hypoxia following atherosclerosis, cardiac or cerebral infarction, tumour promotion, inflammation, ischaemia, alterations of the synovial liquid, collagen degradation, among others. The method consists in administering to said animals and especially to human beings an amount, efficient against said effects, of a plant extract with a proanthocyanidins content which has a radical scavenger effect, the extract being in the form of a medicament and coming more especially from the bark of conifers.

OTHER PUBLICATIONS

T. A. Geissman and N. N. Yoshimura (1966) "Synthetic Proanthocyandin", *Tetrahedron Letters*, 24:2669–2673 (Exhibit 11).

P. Gendre, J. Laparra and E. Barraud (1985) "Effet protecteur des oligomeres procyanidoliques sur le lathyrisme experimental chez le Rat", *Ann. Pharmaceutiques francaises*, 43: 61–71 (Exhibit 12).

E. Haslam, "Proanthocyanids", *The Flavonoids: Advances in Research*, Chapman and Hall, New York, 417–437 (Exhibit 13).

E. Haslam, "Natural Proanthocyanidins", *The Flavonoids*, Chapman and Hall, New York, 505–559 (Exhibit 14).

J. Laparra, J. Michaud, M.F. Lesca, P. Blanquet and J. Masquelier (1978) "Etude Pharmacocinetique des Oligomeres Procyanidoliques totaux du Raisin", *Acta Therapeutica* 4: 233–246 (Exhibit 15).

J. Laparra, J. Michaud and J. Masquelier (1979) "Action des Oligomeres Procyanidoliques sur le Cobaye Carence en Vitamine C", *Reproduction interdite sans indication de souree*, 7–13 (Exhibit 16).

J. Laparra, J. Michaud and J. Masquelier (1977) "Etude pharmacocinetique des oligomeres flavanoliques", *Plantes medicinales et phytotherapie*, 11: 133–142 (Exhibit 17).

J. Lavollay and J. Neumann (1959) "Problems Posed by the Activity of Certain Flavonoids on Vascular Resistance", *The Pharmacology of Plant Phenolics*, 103–122 (Exhibit 18).

A. Letan (1966) "The Relation of Structure to Antioxidant Activity of Quercetin and Some of Its Derivatives I. Primary Activity", *Journal Of Food Science*, 31: 518–523 (Exhibit 19).

A. Letan (1966) "The Relation of Structure to Antioxidant Activity of Quercitin and Some of Its Derivatives II. Secondary (Metal-Complexing) Activity", *Journal of Food Science*, 31: 395–399 (Exhibit 20).

I. Maridonneau P. Braquet and R. P. Garay, (1981) "Bioflavonoids protect human erthrocytes against the K+-loss induced by free radicals", *Proceedings of the International Bioflavonoid Symposium*, Munich, FRG, Munich, 427–436 (Exhibit 21).

J. Masquelier (1963) "Dosage des Leucoanthocyannes du Vin Blanc Emploi de la Poudre de Polyamide" *Bull Soc. Pharm. Bordeaux*, 102: 31–32 (Exhibit 22).

Jack Masquelier (1948) "Etude Biologique du Chromogene", *Recherches sur le Pigments de la Graine D'Arachide*, Bordeaux, 84–101 (Exhibit 23).

J. Masquelier (1972) "La Vitamine C2", *Extrait des Journees Pharmaceutiques Internationals de Paris*, 3–12 (Exhibit 24).

Masquelier (1980) "Pycnogenols: Recent Advances in the Therapeutical Activity of Procyanidins", *Natural Products as Medicinal Agents, Plenary Lectures of the International Research Congress on Medicinal Plant Research*, Strasbourg, 243–256 (Exhibit 25).

Jack Masquelier,(1948) *Recherches sur les Pigments de la Grains D'Arachide* Bordeaux, 1–117 (Exhibit 26).

Jack-Arthur Masquelier, No. 1.036.922 (1953) "Procede d'extraction du leucocyanidol", *Brevet D'Invention*, Francaise (Exhibit 27).

J. Masquelier, M.C. Dumon and J. Dumas, (1981) "Stabilisation du collagene par les oligomeres procyanidoliques", *Acta Therapeutica*, 7: 101–5 (Exhibit 28).

J. Masquelier and J. Golse, (1961) "Presence du Complexe Leucocyanidol Catechine de Forsyth dans le Chocolat", *Bull, Soc., Pharm., Bordeaux*, 100: 241–247 (Exhibit 29).

J. Masquelier and J. Michaud, (1965) "Etat des Leucoanthocyannes Dans le Rhytidome de Pinus Maritima Lamk", *Bul. Soc. Pharm.* Bordeaux, 104: 33–36 (Exhibit 30).

J. Masquelier, J. Michaud, J. Laparra and M. C. Dumon, (1979) "Flavonoids and Pycnogenols", *International Journal for Vitamin and Nutrition Research*, 49: 307–311 (Exhibit 31).

J. Masquelier, J. Michaud and J. Triaud, (1965) "Fractionnement des Leucoanthocyannes du Vin" *Bulletin de la Societe de Pharmacie de Bordeaux*, 104: 85 (Exhibit 32).

J. Masquelier and G. Point (1956) "Le Leucoanthocyane des Cepages Blancs de Vitis Vinifera", *Bull. Soc. Pharm. Bordeaux*, 95: 6–11 (Exhibit 33).

J. Masquelier and G. Point (1956) "Les Substances Vitaminiques P des vins Blancs Extraction et Dosage", *Bulletin de la Societe de Pharmacie de Bordeaux*, 80–84 (Exhibit 34).

J. Masquelier and J. Roux (1960) "Sur la Stabilite des Leucoanthocyannes dans les Medicaments Galeniques", *Bull. Soc. Pharm. Bordeaux*, 65–72 (Exhibit 35).

J. Masquelier and G. Sansous (1953) "Un Nouveau Facteur Vitaminique P Isole du Pin des Landes", *Bulletin de la Societe de Pharmacie*, 91: 16–19 (Exhibit 36).

J. Masquelier and F. Tayeau.(1950) "Recherches Comparatives sur L'Activite de Diverses Substances Vitaminiques P", *Societe de Pharmacie*, 88: 168–171 (Exhibit 37).

J. Masquelier, G. Vitte and M. Ortega (1959) "Dosage Colorimetriques des Leucoanthocyannes dans les vins Rouges", *Bull. Soc. Pharm. Bordeaux*, 98: 145–148 (Exhibit 38).

S.M. de Matta, F.D. Monache, F. Ferrari and G.B. Marini-Bettolo (1975) "Alkaloids and Procyanidins of an Unicaria sp. From Peru", *Il Farmaco*, 31: 527–535 (Exhibit 39).

J. Michaud, P. Lacaze and J. Masquelier, (1971) "Fractionnement des Oligomeres Flavanoliques du Raisin", *Bull, Soc. Pharm. Bordeaux*, 110: 111–116 (Exhibit 40).

J. Michaud, J. Laparra, M.F. Lesca, M.F. Armand, J. Masquelier and P. Blanquet, (1969) "Phytosynthese de Rutoside Marque au C", *Soc. Pharm. Bordeaux*, 108: 133–142 (Exhibit 41).

J. Michaud, J. Laparra, M.F. Lesca, P. Blanquet and J. Masquelier, (1977) "Preparation D'Oligomeres Procyanidoliques de Vitis Vinifera L. Marques au C", *Bull. Soc. Pharm. Bordeaux*, 116: 21–26(Exhibit 42).

J. Michaud and J. Masquelier, (1973) "Quelques aspects nouveaux de la connaissance des tanins catechiques leurs relation avec la vitamine C2(P)", *Prod. Et Prob. Pharm.*, 28: 499–520 (Exhibit 43).

J. Michaud, J. Masquelier and M.C. Dumon, (1981) "Etude analytique des tanins catechiques", *Bull. Soc. Pharm. Bordeaux*, 120: 63–74 (Exhibit 44).

J. Michaud, J. Masquelier and A.M. Roudge, (1973) "Synthese des procyanidines naturelles", *Annales pharmaceutiques francaises*, 31: 385–395 (Exhibit 45).

Elliott Middleton Jr., (1984) "The Flavonoids", *TIPS*, 335–338 (Exhibit 46).

J. Monboisse, P. Braquet, A. Randoux and J.P. Borel, (1983) "Non–Enzymatic Degradation of Acid–Soluble Calf Skin Collagen By Superoxide Ion: Protective Effect of Flavonoids", *Biochemical Pharmacology*, 32: 53–8 (Exhibit 47).

N. Nikolov, H. Wagner, J. Chopin, G. Dellamonica, V.M. Chari and O. Seligmann, (1981) "Recent Investigations of Crataegus Flavonoids", *Proceedings Of the International Bioflavonoid Symposium* Munich, FRG, 325–344 (Exhibit 48).

Kazuhiko Nozaki, Tadae Kushida, Tomoyoshi Nakajima, Mizuo Yajima and Koki Yokotsuka, (1984) "Antioxidant Activities of Phenolic Compounds from Seeds and Skins of 33 Grape Varieties", *Yamanashi University*, Tokyo (Exhibit 49 with English Translation).

Brigitte Pignatelli, Jean–Claude Bereziat, Gerard Descotes and Helmut Bartsch, (1982) "Catalysis of nitrosation in vitro and in vivo in rats by catechin and esorcinol and inhibition by chlorogenic acid", *Carcinogenesis*, 3: 1045–1049 (Exhibit 50).

Dan E. Pratt, (1975) "Role of Flavones and Related Compounds in Retarding Lipid–Oxidative Flavor Changes in Foods" ACS Symposium Series, Washington, D.C. (Exhibit 51).

V. W. Rewerski, T. Piechocki, M. Rylski and S. Lewak, (1971) "Einige pharmakologische Eigenschaften der aus Weissdorn (Crataegus oxyacantha) isolierten oligomeren Procyanidine" *Arzneim.–Forsch*, 21: 886–888 (Exhibit 52).

Von C. Roddewig and H. Hensel, (1977) "Reaktion der lokalen Myodkarddurchblutung von wachen Hunden und narkotisierten auf orale und parenterale Applikation einer Crataegudfraktion (oligomere Procyanidine)", *Arzneim.–Forsch.*, 7: 1407–1410 (Exhibit 53).

Otto Rosenheim, (1920) "Observations on anthocyanins. I. The Anthocyanins of the young leaves of the grape vine.", *The Biochemical Journal*, XIV: 178–188 (Exhibit 54).

R. Salvayre, P. Braquet, Th. Perruchot and L. Douste–Blazy, (1981) "Comparison of the Scavenger Effect of Bilberry Anthocyanides with Various Flavonoids", *Proceedings of the International Bioflavonoid Symposium*, Munich FRG, 437–442 (Exhibit 55).

J. Schmidtke and V. Schoop, (1984) "Das hydrostatische Oedem und seine medikamentoese Beeinflussung", *Scheuzerische Geseelschaft fur Phlebologie* (Exhibit 56).

J. Sipos, V. Gabor, Z. Toth and P. Ribiczey, (1984) "Effect to (+)–Cyanidanol–3 on Receptor Activity of Lymphocytes and Hepatocytes and on Hepatocyte–Lymphocyte Conjugation in Alcoholic Liver Disease", *Int. J. Tiss Reac.*, VI(2): 145–154 (Exhibit 57).

N. P. Slabbert, (1977) "Ionisation of some flavanols and dihydroflavonols", *Tetrahedron*, 33: 821–824 (Exhibit 58).

Societe Civile de Recherche Pharmaceutique et Therapeutique No. 4482, (1966) "Nouveau bioflavonoide ou facteur vitaminique P", Bulletin officiel de la Propriete industrielle, 45: 1966 (Exhibit 59).

Societe Civile de Recherche Pharmaceutique et Therapeutique No. 1.427.100, (1966) "Procede pour l'obtention d'hydroxyflavanne–3–4–diols", Bulletin de la Propriete industrielle, 6: 1966 (Exhibit 60).

T. Swain, (1965) "Analytical Methods for Flavonoids", *Chemistry and Biochemistry of Plant Pigments*, 533–549 (Exhibit 61).

F. Tayeau and J. Masquelier, (1949) "Les Pigments de la graine d'Arachide", *Bulletin de la Societe de Chimie biologique*, 31: 72–5 (Exhibit 62).

J. M. Tixier, G. Godeau, A.M. Robert and W. Hornbeck, (1984) "Evidence by in vivo and in Studies that Binding of Pycnogenols to Elastin Affects its Rate of Degradation By Elastases", *Biochemical Pharmacology*, 33: 3933–3939 (Exhibit 63).

Shinji Uchida, Rei Edamatsu, Midori Hiramatsu, Akitane Mori, Gen–ichiro Nonaka, Itsuo Nishioka, Masami Niwa and Masayori Ozaki, (1987) "Condensed tannins scavenge active oxygen free radicals", *Medical Science Research*, 15: 831 (Exhibit 64).

L. A. Videla, (1983) "Assessment of the scavenging action of reduced gluthathione, (+)–cyanidanol–3 and ethanol by the chemiluminescent response of the xanthine oxidase reaction", *Experientia*, 39: 500–502 (Exhibit 65).

U. K. Weinges, P. Kloss and H. Jaggy, (1972) "Uber dimere und oligomere Dehydrocatechine", catechine, *Arzneim.–Forsch.*, 22: 166–168 (Exhibit 66).

C.P. Siegers and M. Younes, (1981) "Effects of Bioflavonoids on Lipid Peroxidation Induced By Glutathione Depletion", *Proceedings of the International Bioflavonoid Symposium*, Munich FRG, 403–409. (Exhibit 68).

T. F. Slater and M.N. Eakins, (1974) "Interactions of (+)–Cyanidol–3 with Free Radical Generating Systems" *International Symposium in New Trends in the Therapy of Liver Diseases*, 84–49. (Exhibit 69).

Kolodziej, et al. (1981) "Structure Elicidation and Hindered Rotation of Two Procyanidins From Nelie Meyeri" *Proceedings of the International Bioflavonoid Symposium*, 353–362. (Exhibit 70).

J. Masquelier, J. Michaud, J. Laparra and M.C. Dumon, (1979) "Pycnogenols" *Bull. Soc. Pharm. Bordeaux*, 118: 95–108. (Exhibit 71).

I. Ueno, M. Kohno, K. Haraikawa and I Hirono, (1984) "Interaction Between Quercetin and Superoxide Radicals. Reduction of the Quercitin Mutagenicity" *Journal of Pharmacobio–Dynamics*, 798–803. (Exhibit 72).

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–7 is confirmed.

* * * * *